US009050174B2

(12) United States Patent
Pecor et al.

(10) Patent No.: US 9,050,174 B2
(45) Date of Patent: Jun. 9, 2015

(54) DEFLATION AND REMOVAL OF IMPLANTABLE MEDICAL DEVICES

(75) Inventors: Robert Pecor, Aliso Viejo, CA (US); Jason Kwok, Anaheim, CA (US); Mark Ashby, Laguna Niguel, CA (US)

(73) Assignee: ReShape Medical, Inc., San Clemente, CA (US)

( * ) Notice: Subject to any disclaimer, the term of this patent is extended or adjusted under 35 U.S.C. 154(b) by 548 days.

(21) Appl. No.: 13/386,638

(22) PCT Filed: Jul. 23, 2010

(86) PCT No.: PCT/US2010/043136
§ 371 (c)(1),
(2), (4) Date: Mar. 29, 2012

(87) PCT Pub. No.: WO2011/011743
PCT Pub. Date: Jan. 27, 2011

(65) Prior Publication Data
US 2012/0184981 A1    Jul. 19, 2012

Related U.S. Application Data

(60) Provisional application No. 61/228,081, filed on Jul. 23, 2009.

(51) Int. Cl.
*A61F 5/00*     (2006.01)
*A61M 25/00*   (2006.01)
*A61M 25/10*   (2013.01)

(52) U.S. Cl.
CPC .......... *A61F 5/0089* (2013.01); *A61M 25/0068* (2013.01); *A61M 25/007* (2013.01); *A61M 2025/0079* (2013.01); *A61M 2025/0095* (2013.01); *A61M 2025/1054* (2013.01)

(58) Field of Classification Search
CPC .......... A61M 25/0068; A61M 25/007; A61M 2025/1054; A61M 2025/0079; A61M 2025/0095; A61F 5/0089
USPC ................. 606/127, 128, 184, 185, 192, 194; 604/22, 164.01, 164.02, 96.01, 97.01
See application file for complete search history.

(56) References Cited

U.S. PATENT DOCUMENTS 2,493,326 A    1/1950   Trinder
4,133,315 A    1/1979   Berman et al.
(Continued)

FOREIGN PATENT DOCUMENTS

DE    8708978 U1    11/1987
EP    0103481        3/1984
(Continued)

OTHER PUBLICATIONS

Extended European Search Report; Application No. EP11766679.2, Applicant: Reshape Medical, Inc., mailed Dec. 12, 2013, 6 pages.
(Continued)

*Primary Examiner* — Julian W Woo
*Assistant Examiner* — Lucas Paez
(74) *Attorney, Agent, or Firm* — Perkins Coie LLP (57) ABSTRACT

A deflation catheter device, comprising: a catheter tube having a proximal end and a distal end; a stylet disposed within the catheter tube; a stylet handle attached to the stylet; and a y-connector disposed near a proximal end of the catheter tube, configured to provide fluid communication from the distal end of the catheter tube and a suction port, and configured to provide access for the stylet from the proximal end of the catheter tube to the distal end of the catheter tube.

6 Claims, 4 Drawing Sheets

(56) References Cited

U.S. PATENT DOCUMENTS

| | | | |
|---|---|---|---|
| 4,246,893 A | 1/1981 | Berson | |
| 4,356,824 A | 11/1982 | Vazquez | |
| 4,416,267 A | 11/1983 | Garren et al. | |
| 4,465,072 A * | 8/1984 | Taheri | 606/159 |
| 4,485,805 A | 12/1984 | Foster, Jr. | |
| 4,598,699 A | 7/1986 | Garren et al. | |
| 4,694,827 A | 9/1987 | Weiner et al. | |
| 4,723,547 A * | 2/1988 | Kullas et al. | 606/185 |
| 4,899,747 A | 2/1990 | Garren et al. | |
| 4,940,458 A | 7/1990 | Cohn | |
| 5,073,347 A | 12/1991 | Garren et al. | |
| 5,084,061 A | 1/1992 | Gau et al. | |
| 5,123,840 A | 6/1992 | Nates | |
| 5,234,454 A | 8/1993 | Bangs | |
| 5,259,399 A | 11/1993 | Brown | |
| 5,263,934 A | 11/1993 | Haak | |
| 5,273,536 A | 12/1993 | Savas | |
| 5,318,530 A | 6/1994 | Nelson, Jr. | |
| 5,334,187 A | 8/1994 | Fischell et al. | |
| 5,431,173 A | 7/1995 | Chin et al. | |
| 5,496,271 A | 3/1996 | Burton et al. | |
| 5,575,772 A | 11/1996 | Lennox | |
| 5,643,209 A | 7/1997 | Fugoso et al. | |
| 5,730,722 A | 3/1998 | Wilk | |
| 5,779,728 A | 7/1998 | Lunsford et al. | |
| 5,857,991 A | 1/1999 | Grothoff et al. | |
| 5,876,376 A | 3/1999 | Schwab et al. | |
| 5,938,669 A | 8/1999 | Klaiber et al. | |
| 5,993,473 A | 11/1999 | Chan et al. | |
| 6,149,621 A | 11/2000 | Makihara | |
| 6,254,355 B1 | 7/2001 | Gharib | |
| 6,276,567 B1 | 8/2001 | Diaz et al. | |
| 6,280,411 B1 | 8/2001 | Lennox | |
| 6,423,058 B1 | 7/2002 | Edwards et al. | |
| 6,427,089 B1 | 7/2002 | Knowlton | |
| 6,454,785 B2 | 9/2002 | De Hoyos Garza | |
| 6,524,234 B2 | 2/2003 | Ouchi | |
| 6,535,764 B2 | 3/2003 | Imran et al. | |
| 6,547,788 B1 | 4/2003 | Maguire et al. | |
| 6,579,301 B1 | 6/2003 | Bales et al. | |
| 6,592,552 B1 * | 7/2003 | Schmidt | 604/164.01 |
| 6,613,018 B2 | 9/2003 | Bagga et al. | |
| 6,613,037 B2 | 9/2003 | Khosravi et al. | |
| 6,706,010 B1 | 3/2004 | Miki et al. | |
| 6,746,460 B2 | 6/2004 | Gannoe et al. | |
| 6,826,428 B1 | 11/2004 | Chen et al. | |
| 6,850,128 B2 | 2/2005 | Park | |
| 6,866,657 B2 | 3/2005 | Shchervinsky | |
| 6,869,431 B2 | 3/2005 | Maguire et al. | |
| 6,890,300 B2 | 5/2005 | Lloyd et al. | |
| 6,890,346 B2 | 5/2005 | Ganz et al. | |
| 6,902,535 B2 * | 6/2005 | Eberhart et al. | 600/585 |
| 6,923,754 B2 | 8/2005 | Lubock | |
| 6,931,286 B2 * | 8/2005 | Sigg et al. | 607/120 |
| 6,939,299 B1 | 9/2005 | Petersen et al. | |
| 6,958,052 B1 | 10/2005 | Charlton | |
| 7,001,419 B2 | 2/2006 | DiCaprio et al. | |
| 7,016,735 B2 | 3/2006 | Imran et al. | |
| 7,020,531 B1 | 3/2006 | Colliou et al. | |
| 7,033,373 B2 | 4/2006 | de la Torre et al. | |
| 7,056,305 B2 | 6/2006 | Garza Alvarez | |
| 7,076,305 B2 | 7/2006 | Imran et al. | |
| 7,081,125 B2 * | 7/2006 | Edwards et al. | 606/213 |
| 7,131,945 B2 | 11/2006 | Fink et al. | |
| 7,483,746 B2 | 1/2009 | Lee et al. | |
| 7,625,355 B2 * | 12/2009 | Yu | 604/164.01 |
| 7,828,749 B2 | 11/2010 | Douglas et al. | |
| 8,083,757 B2 | 12/2011 | Gannoe et al. | |
| 2001/0022988 A1 | 9/2001 | Schwarz et al. | |
| 2001/0037127 A1 | 11/2001 | De Hoyos Garza | |
| 2002/0055757 A1 | 5/2002 | Torre et al. | |
| 2002/0107515 A1 | 8/2002 | Edwards et al. | |
| 2002/0161388 A1 | 10/2002 | Samuels et al. | |
| 2002/0173804 A1 | 11/2002 | Rousseau | |
| 2003/0114878 A1 | 6/2003 | Diederich et al. | |
| 2003/0171768 A1 | 9/2003 | McGhan | |
| 2003/0187390 A1 | 10/2003 | Bates et al. | |
| 2004/0044354 A1 | 3/2004 | Gannoe et al. | |
| 2004/0059289 A1 | 3/2004 | Garza Alvarez | |
| 2004/0059290 A1 | 3/2004 | Palasis | |
| 2004/0073162 A1 | 4/2004 | Bleam et al. | |
| 2004/0087902 A1 | 5/2004 | Richter | |
| 2004/0106899 A1 | 6/2004 | McMichael et al. | |
| 2004/0116897 A1 | 6/2004 | Aboul-Hosn | |
| 2004/0127915 A1 | 7/2004 | Fleenor et al. | |
| 2004/0186502 A1 | 9/2004 | Sampson et al. | |
| 2004/0220665 A1 | 11/2004 | Hossainy et al. | |
| 2004/0236280 A1 | 11/2004 | Rice et al. | |
| 2004/0236361 A1 | 11/2004 | Sakurai | |
| 2004/0254600 A1 | 12/2004 | Zarbatany et al. | |
| 2005/0027283 A1 | 2/2005 | Richard et al. | |
| 2005/0027313 A1 | 2/2005 | Shaker | |
| 2005/0038415 A1 | 2/2005 | Rohr et al. | |
| 2005/0055039 A1 | 3/2005 | Burnett et al. | |
| 2005/0059990 A1 | 3/2005 | Ayala et al. | |
| 2005/0075624 A1 | 4/2005 | Miesel | |
| 2005/0085792 A1 | 4/2005 | Gershowitz | |
| 2005/0119674 A1 | 6/2005 | Gingras | |
| 2005/0131442 A1 | 6/2005 | Yachia et al. | |
| 2005/0143784 A1 | 6/2005 | Imran | |
| 2005/0159769 A1 | 7/2005 | Alverdy | |
| 2005/0177103 A1 | 8/2005 | Hunter et al. | |
| 2005/0192615 A1 | 9/2005 | Torre et al. | |
| 2005/0267595 A1 | 12/2005 | Chen et al. | |
| 2005/0267596 A1 | 12/2005 | Chen et al. | |
| 2005/0273060 A1 | 12/2005 | Levy et al. | |
| 2006/0058829 A1 | 3/2006 | Sampson et al. | |
| 2006/0178691 A1 | 8/2006 | Binmoeller | |
| 2006/0184112 A1 | 8/2006 | Horn et al. | |
| 2006/0259020 A1 | 11/2006 | Sharratt | |
| 2007/0016262 A1 | 1/2007 | Gross et al. | |
| 2007/0093728 A1 | 4/2007 | Douglas et al. | |
| 2007/0100367 A1 | 5/2007 | Quijano et al. | |
| 2007/0100368 A1 | 5/2007 | Quijano et al. | |
| 2007/0100369 A1 | 5/2007 | Cragg et al. | |
| 2007/0142770 A1 | 6/2007 | Rioux et al. | |
| 2007/0149994 A1 | 6/2007 | Sosnowski et al. | |
| 2007/0173881 A1 | 7/2007 | Birk et al. | |
| 2007/0233161 A1 | 10/2007 | Weller et al. | |
| 2007/0250020 A1 | 10/2007 | Kim et al. | |
| 2007/0265369 A1 | 11/2007 | Muratoglu et al. | |
| 2007/0265598 A1 | 11/2007 | Karasik | |
| 2007/0288033 A1 * | 12/2007 | Murature et al. | 606/106 |
| 2008/0082056 A1 | 4/2008 | Mauch et al. | |
| 2008/0085887 A1 | 4/2008 | Didiuk et al. | |
| 2008/0097513 A1 | 4/2008 | Kaji et al. | |
| 2008/0119729 A1 | 5/2008 | Copa et al. | |
| 2008/0172079 A1 | 7/2008 | Birk | |
| 2008/0190363 A1 | 8/2008 | Chen et al. | |
| 2008/0208241 A1 | 8/2008 | Weiner et al. | |
| 2008/0233167 A1 | 9/2008 | Li et al. | |
| 2008/0243071 A1 | 10/2008 | Quijano et al. | |
| 2008/0243166 A1 | 10/2008 | Paganon et al. | |
| 2008/0255601 A1 | 10/2008 | Birk | |
| 2008/0319471 A1 | 12/2008 | Sosnowski et al. | |
| 2009/0048624 A1 | 2/2009 | Alverdy | |
| 2009/0259236 A2 | 10/2009 | Burnett et al. | |
| 2009/0275973 A1 | 11/2009 | Chen et al. | |
| 2010/0023047 A1 | 1/2010 | Simpson | |
| 2010/0130998 A1 | 5/2010 | Alverdy | |
| 2010/0243135 A1 | 9/2010 | Pepper et al. | |
| 2010/0251837 A1 | 10/2010 | Bouasaysy et al. | |
| 2011/0178544 A1 | 7/2011 | Sosnowski et al. | |
| 2012/0271336 A1 | 10/2012 | Hamman et al. | |
| 2012/0289992 A1 | 11/2012 | Quijano et al. | |

FOREIGN PATENT DOCUMENTS

| | | |
|---|---|---|
| EP | 0457456 A1 | 11/1991 |
| EP | 0485903 A2 | 5/1992 |
| EP | 1781183 | 5/2007 |
| FR | 2862525 A1 | 5/2005 |
| FR | 2892297 | 4/2007 |
| GB | 2139902 A | 11/1984 |

(56) References Cited

FOREIGN PATENT DOCUMENTS

| | | |
|---|---|---|
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| WO | WO-0141700 | 6/2001 |
| WO | WO-0166166 A2 | 9/2001 |
| WO | WO-0240081 | 5/2002 |
| WO | WO-2006035446 A2 | 4/2006 |
| WO | WO-2006056944 A1 | 6/2006 |
| WO | WO-2006/128978 A1 | 12/2006 |
| WO | WO 2007027812 A2 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO-2008121831 A1 | 10/2008 |
| WO | WO-2009055386 A2 | 4/2009 |
| WO | WO-2009112786 A2 | 9/2009 |
| WO | WO-2010048021 | 4/2010 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011024077 A2 | 3/2011 |
| WO | WO-2011038270 A2 | 3/2011 |
| WO | WO-2011097637 A1 | 8/2011 |
| WO | WO-2011127205 A1 | 10/2011 |
| WO | WO2012048226 | 4/2012 |

OTHER PUBLICATIONS

Extended European Search Report; Application No. EP11748141.6, Applicant: Reshape Medical, Inc., mailed Feb. 25, 2014, 6 pages.

Non-Final Office Action; U.S. Appl. No. 12/723,545, date Feb. 29, 2012, 10 pages.

European Supplementary Search Report; EP Application No. 10802994.3, Applicant: ReShape Medical, Inc., mailed Jun. 28, 2013, 8 pgs.

European Supplementary Search Report; EP Application No. 10802918.2, Applicant: ReShape Medical, Inc., mailed Jun. 5, 2013, 6 pgs.

Non-Final Office Action; U.S. Appl. No. 11/263,302; dated: Oct. 9, 2012, 6 pages.

Non-Final Office Action; U.S. Appl. No. 12/625,473; dated Jul. 12, 2012; 10 pages.

Non-Final Office Action; U.S. Appl. No. 12/753,751; dated Oct. 5, 2012, 8 pages.

Non-Final Office Action; U.S. Appl. No. 13/074,956; dated Oct. 1, 2012, 8pages.

Final Office Action; U.S. Appl. No. 11/694,536, Mailing Date Mar. 11, 2011, 13 pages.

Final Office Action; U.S. Appl. No. 11/768,152, Mailing Date Jan. 19, 2011, 13 pages.

International Search Report; International Application No. PCT/US2010/042948; Applicant: ReShape Medical, Inc., Mailing Date Apr. 1, 2011, 11 pages.

International Search Report; International Application No. PCT/US2010/043134; Applicant: ReShape Medical, Inc., Mailing Date Apr. 27, 2011, 12 pages.

International Search Report; International Application No. PCT/US2010/043136; Applicant: ReShape Medical, Inc., Mailing Date Apr. 12, 2011, 9 pages.

International Search Report; International Application No. PCT/US2010/050260; Applicant: ReShape Medical, Inc., Mailing Date: Jun. 17, 2011, 9 pages.

International Search Report; International Application No. PCT/US2011/026233; Applicant: ReShape Medical, Inc., Mailing Date Apr. 26, 2011, 9 pages.

International Search Report; International Application No. PCT/US2011/031463; Applicant: ReShape Medical, Inc., Mailing Date: Jun. 27, 2011, 10 pages.

International Search Report; International Application no. PCT/US2003/012782, Applicant: Applied Medical Resources Corporation, Mailing Date Oct. 28, 2003, 7 pages.

International Search Report; International Application No. PCT/US2006/042336, Applicant: Abdominus, Inc., Mailing Date Mar. 14, 2007, 9 pages.

International Search Report; International Application No. PCT/US2006/042710, Applicant: Abdominus, Inc. et al., Mailing Date Mar. 15, 2007, 9 pages.

International Search Report; International Application No. PCT/US2006/042711, Applicant: Abdominus, Inc. et al, Mailing Date Mar. 16, 2007, 9 pages.

International Search Report; International Application No. PCT/US2006/048647, Applicant: Abdominus, Inc. et al., Mailing Date May 22, 2007, 12 pages.

International Search Report; International Application No. PCT/US2008/058677, Applicant: ReShape Medical et al., Mailing Date Aug. 21, 2008, 12 pages.

International Search Report; International Application No. PCT/US2008/068058, Applicant: ReShape Medical, Inc. et al, Mailing Date Nov. 19, 2008, 11 pages.

International Search Report; International Application No. PCT/US2010/029865, Applicant: ReShape Medical, Inc., Mailing Date Jan. 5, 2011, 9 pages.

International Search Report; International Application No. PCT/US2011/024077; Applicant: ReShape Medical, Inc., Mailing Date Apr. 6, 2011, 12 pages.

International Search Report; International Application No. PCT/US2011/024082, Applicant: ReShape Medical, Inc., Mailing Date Apr. 6, 2011, 10 pages.

International Search Report and Written Opinion; International Applicaton No. PCT/US1155373, Applicant: Reshape Medical, Inc., Mailing Date Jan. 20, 2012, 7 pages.

Non-Final Office Action; U.S. Appl. No. 11/694,536; Mailing Date Oct. 26, 2011, 13 pages.

Non-Final Office Action; U.S. Appl. No. 12/625,473; Mailing Date Oct. 24, 2011, 18 pages.

Patient Information "Living with the BIB" by INAMED Health (2004).

"Reshape Inflatable Gastric Ballon Going on Trial as Weight Loss Option," MedGadget: Internet Journal of Emerging Medical Technologies. Feb. 4, 2010. (5 pages).

Supplementary European Search Report for EP 03726447.0, mailed Mar. 1, 2006.

Wahlen CH et al. "The BioEnterics Intragastric Balloon: How to use it" Obesity Surgery 2001; 11:524-527.

Non-Final Office Action; U.S. Appl. No. 13/386,650; mailed on Jun. 3, 2014, 15 pages.

Ostrovsky, ReShape Inflatable Gastric Balloon going on Trial as Weight Loss Option; http://www.medgadget.com/2010/02/reshape__inflatable__gastric__balloon__system__going__on__trial__as__weight__loss__option.html Feb. 4, 2010, retrieved on 02-10-2-13.

Notice of Allowance; U.S. Appl. No. 12/753,803, dated May 13, 2014, 18 pages.

Extended European Search Report; Application No. EP11831683.5, Applicant: Reshape Medical, Inc., mailed Jul. 3, 2014, 8 pages.

Final Office Action; U.S. Appl. No. 13/556,032, mailed on Jan. 28, 2014, 8 pages.

Final Office Action; U.S. Appl. No. 13/858,767, Mailing Date May 22, 2013, 12 pages.

Extended European Search Report; Application No. EP6827098.3, Applicant: Reshape Medical, Corporation, mailed on Aug. 25, 2014, 3 pages.

(56) References Cited

OTHER PUBLICATIONS

Extended European Search Report; Application No. EP6827314.3, Applicant: ReShape Medical Corporation, mailed Aug. 1, 2014, 3 pages.
Extended European Search Report; Application No. EP6827313.5, Applicant: ReShape Medical Corporation, mailed Jul. 30, 2014, 5 pages.
Extended European Search Report; application No. EP6847847.8, Applicant ReShape Medical Corporation, mailed Aug. 14, 2014, 5 pages.
Final Office Action; U.S. Appl. No. 13/858,767, mailed on May 30, 2014, 12 pages.
Non-Final Office Action; U.S. Appl. No. 13/386,638, mailed on Jun. 27, 2014, 12 pages.
Extended European Search Report; Application No. EP11740536.5, Applicant: ReShape Medical, Inc., mailed Jul. 3, 2014, 8 pages.

\* cited by examiner

DEFLATION AND REMOVAL OF IMPLANTABLE MEDICAL DEVICES

RELATED APPLICATION

The present application is a U.S. National Phase application under 35 U.S.C. 371 of International Application Serial No. PCT/US2010/043136, filed Jul. 23, 2010, which claims the benefit of U.S. Provisional Patent Application Ser. No. 61/228,081, filed Jul. 23, 2009, the entire contents of which are incorporated herein by reference in their entireties.

This application incorporates by reference U.S. Pat. Pub. No. 2007/0100368, published May 3, 2007; U.S. Pat. Pub. No. 2007/0100369, published May 3, 2007; U.S. Pat. Pub. No. 2007/0149994, published Jun. 28, 2007; WIPO Pub. No. WO 2007/053556, published Oct. 5, 2007; WIPO Pub. No. WO 2007/053707, published Oct. 5, 2007; WIPO Pub. No. WO 2007/053706, published Oct. 5, 2007; and WIPO Pub. No. WO 2007/075810, published May 7, 2007; WIPO Pub. No. WO/2008/121831, published Oct. 9, 2008; WIPO Pub. No. WO/2009/002989, published Dec. 31, 2008; U.S. patent application Ser. No. 12/723,545, filed Mar. 12, 2010; each as if fully set forth herein in its entirety.

BACKGROUND

This disclosure relates to devices and methods for deflation and removal of implantable medical devices. In particular, this disclosure relates to single or multiple balloon-type gastric space fillers and devices and methods for explant of the same.

SUMMARY

According to embodiments, disclosed is a deflation catheter device, comprising: a catheter tube having a lumen, a proximal end, and a distal end; a stylet disposed within the lumen of the catheter tube and configured to extend beyond the distal end of the catheter tube to puncture a wall of an implanted balloon device; a handle disposed at a proximal end of the catheter tube and attached to the stylet, wherein the handle is configured to controllably advance, retract, and rotate the stylet relative to the catheter tube; and a suction port disposed at a proximal end of the catheter tube and being in fluid communication with the lumen of the catheter tube.

The deflation catheter device may further comprise a seal between the catheter tube and the handle, wherein the stylet crosses the seal from the handle to the lumen of the catheter tube without introducing leaks or pressure losses. The deflation catheter device may further comprise an interface between the handle and a base of the catheter tube configured to guide advancement, retraction, and rotation of the stylet relative to the catheter tube. The interface may be complementary threading. The deflation catheter device may further comprise an aspiration hole providing fluid communication between the interior of a balloon and the catheter tube. The catheter tube and the stylet may define a gap there between at the distal end of the catheter tube, wherein the gap provides fluid communication between the lumen of the catheter tube and an interior of the implanted balloon device while extended within the implanted balloon device. The catheter tube may contain at least one side hole, wherein the at least one side hole provides fluid communication between the lumen of the catheter tube and an interior of the implanted balloon device while extended within the implanted balloon device.

According to embodiments, disclosed is a deflation catheter device, comprising: a catheter tube having a lumen, a proximal end, and a distal end; a hollow needle device disposed within the lumen of the catheter tube and configured to extend beyond the distal end of the catheter tube to puncture a wall of an implanted balloon device; a handle disposed at a proximal end of the catheter tube and attached to the stylet, wherein the handle is configured to controllably advance, retract, and rotate the needle device relative to the catheter tube; and a suction port disposed at a proximal end of the catheter tube and being in fluid communication with the lumen of the catheter tube.

The needle device may further comprise: a sharpened needle tip at a distal end of the needle device; a channel extending axially within the needle device; and an obturator within the channel. A smooth transition from the needle tip to a portion of the obturator may be provided when the obturator is in an extended state. The deflation catheter device may further comprise a spring in the channel tending to place the obturator in the extended state. The sharpened needle tip may be exposed and the smooth transition removed when the obturator is in a retracted state. The obturator may be configured to be retracted by retracting a portion thereof at a proximal end of the catheter tube. The obturator may be configured to be retracted by applying low pressure within the channel relative to a pressure exterior to the channel. The obturator may be configured to be retracted by pressing it against the implanted balloon device.

According to embodiments, disclosed is a method of deflating a balloon, comprising: providing a deflation catheter device comprising a catheter tube and a stylet within the catheter tube; delivering the deflation catheter to an implanted balloon device with the stylet being retracted relative to the distal end of the catheter tube; positioning the catheter tube against a surface of the implanted balloon device; actuating a handle to advance the stylet relative to the catheter tube and the implanted balloon device, whereby the stylet contacts and punctures a wall of the implanted balloon device; advancing at least a portion of the catheter tube through the wall of the implanted balloon device; and aspirating fluid from within the implanted balloon device through the lumen from a distal end thereof to a suction port at a proximal end of the lumen without removing the stylet from the catheter tube.

Actuating the handle may simultaneously rotate the stylet. The method may further comprise: retracting the stylet within the lumen to be concealed by the distal end of the lumen. The method may further comprise: removing the deflation catheter from the balloon. The method may further comprise: reusing the deflation catheter to deflate additional balloons without reloading the stylet into the catheter tube. The method may further comprise: retrieving the implanted balloon device from an implant location.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Various catheter devices having a piercing needle may be used during deflation of intragastric balloon systems to puncture a balloon and aspirate its contents. A catheter device that utilizes a coring mechanism to breach the balloon wall may also be used to aspirate fluid from the balloon. For some of these catheter devices, the needle is connected to a stylet that resides within the catheter tube and has a handle that extends out of a port in the catheter designated for connecting to suction equipment. To puncture the balloon, the handle is pushed forward to advance the needle-tipped stylet into the balloon. It is noted that without any optional control mechanism, the user may accidentally push the handle and expose the needle prematurely. After puncturing the balloon and inserting the catheter through the puncture, the stylet must be removed from the catheter through the port such that suction equipment may be connected to the catheter. In the case that the balloon system has multiple balloons, the stylet is reloaded into the catheter tube or a new catheter device is used in order to puncture additional balloons.

According to embodiments, a novel catheter system is disclosed herein for addressing implantable, inflatable medical devices efficiently, safely, and controllably. The present inventors have developed new catheter devices that allow for puncture and aspiration of fluid from multiple balloons without requiring removal of tools or reconnecting suction tubing and that further provides a controlled advancement and retraction of the needle tip.

According to embodiments, disclosed is deflation catheter device 1 having a proximal end near a user and a distal end near a location of operation. According to embodiments, and as shown in FIGS. 1A, 1B, 1C, and 1D, deflation catheter device 1 comprises a y-connector at or near the proximal end. The y-connector connects a distal segment of catheter tube 10 with two segments: handle 30 and suction port 50. Suction port 50 may connect suction equipment (e.g., a pump or syringe) to catheter tube 10, such that suction port 50 is in fluid communication with the lumen of catheter tube 10. In this manner, access via fluid communication with the distal end of catheter tube 10 is provided at the proximal end thereof.

Figure 1A:
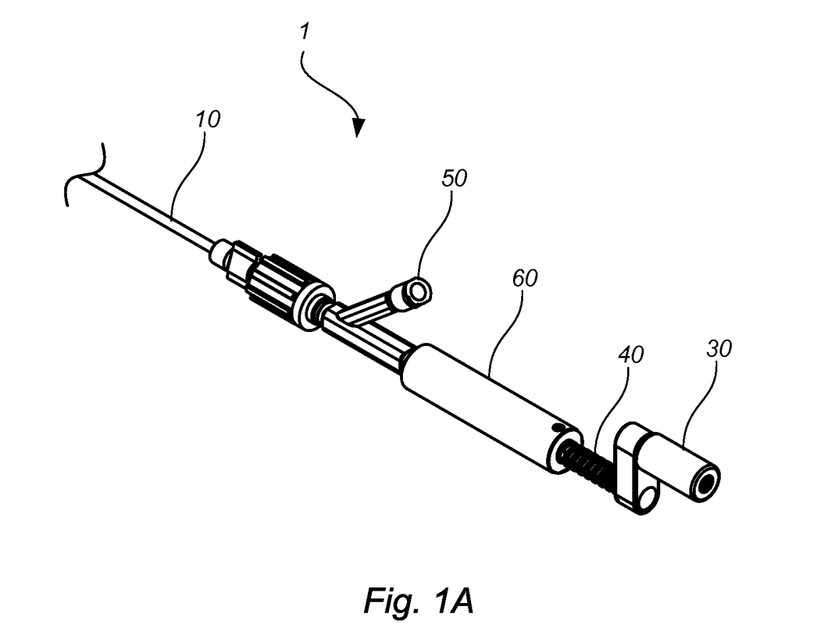
FIG. 1A shows a perspective view of a catheter device.
Figure 1B:
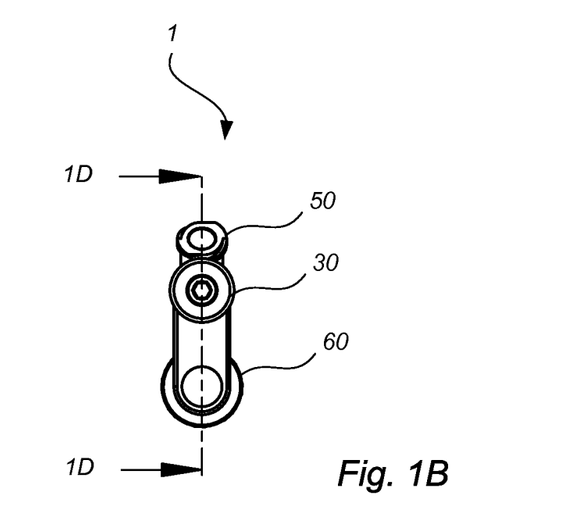
FIG. 1B shows a front view of a catheter device.
Figure 1C:
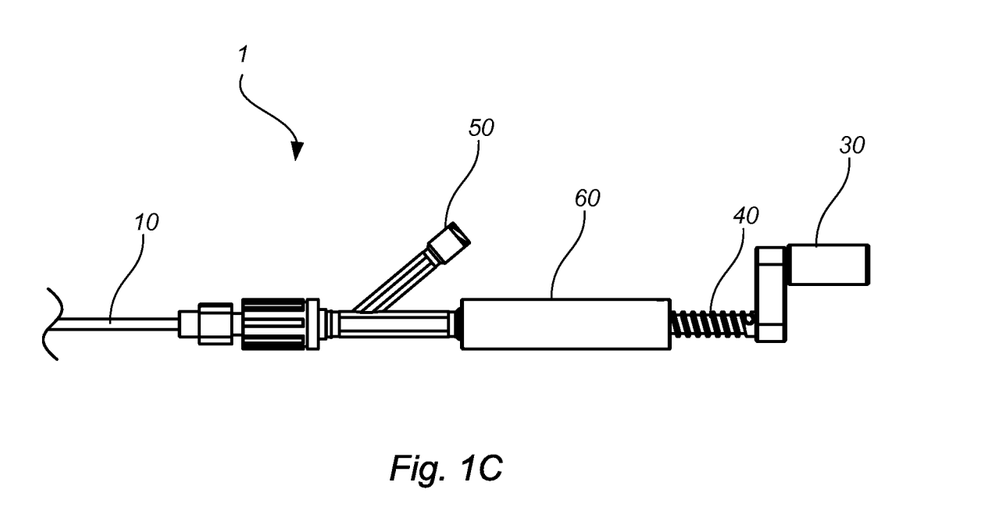
FIG. 1C shows a side view of a catheter device.
Figure 1D:
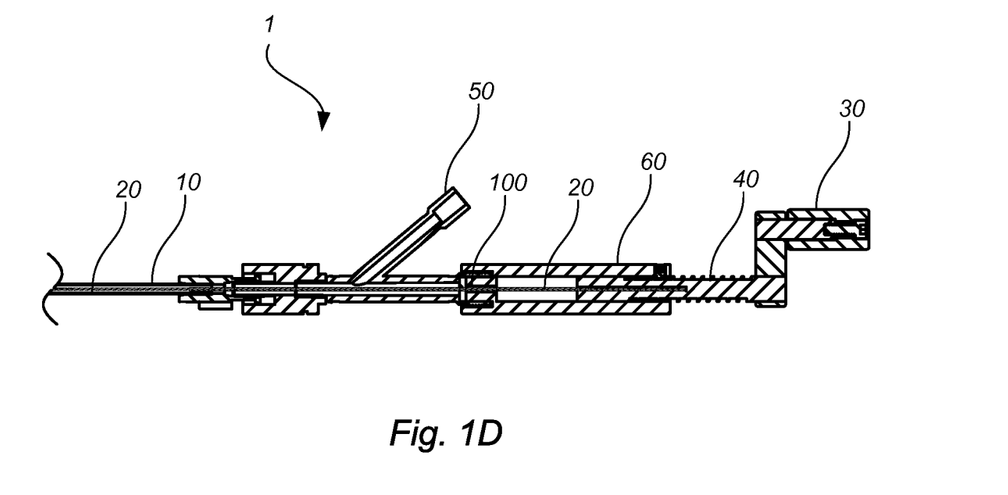
FIG. 1D shows a cross sectional view of a catheter device.

According to embodiments, seal 100 may be provided near suction port 50 to prevent leakage or vacuum loss between the distal portion of catheter tube 10 and another segment connected to the y-connector (e.g., portion containing handle 30). As shown in FIG. 1D, stylet 20 may cross seal 100 from the handle side to the distal segment of catheter tube 10 without allowing leakage or vacuum loss between the distal portion of catheter tube 10 and the handle portion. For example, seal 100 may be configured to allow stylet 20 to pass from the proximal end of catheter tube 10 into the fluid path without allowing leaks around stylet 20. Thus, suction port 50 is provided with exclusive fluid communication access to the lumen of catheter tube 10. This configuration allows for aspiration of fluid through catheter tube 10 without having to remove stylet 20 from the distal segment of catheter tube 10. Also, this enables the user to efficiently puncture and aspirate multiple balloons consecutively because, after deflating one balloon, stylet 20 may simply be retracted to be within catheter tube 10 and advanced again to puncture another balloon without having to entirely reload stylet 20 and risk damaging the catheter.

According to embodiments, interface 40 may be provided for control of stylet 20 relative to catheter tube 10. Interface 40 may allow controlled advancement, retraction, and/or rotation of stylet 20 as well as selective securing of its position relative to catheter tube 10 when not in use.

For example, as shown in FIG. 1, a threaded interface between base 60 of catheter tube 10 and stylet 20 may permit the advancement or retraction of stylet 20 when handle 30 is rotated. According to embodiments, interface 40 may be located proximally or distally along the length of catheter tube 10 (i.e., base 60 thereof). This feature provides for the controlled movement of stylet 20. The ratio of axial travel to the number of rotations may be controlled by the pitch of the threaded interface (for example, approximately 6 threads per inch), which may be optimized for efficient advancement of stylet 20 and consistent puncture of balloons by the rotating stylet 20. The threaded interface may be designed with stops in the threads that limit how far stylet 20 can advance relative to catheter tube 10. For example, stylet 20 may be prohibited from extending beyond approximately 2 cm past the distal tip of the catheter for safety. The threaded interface may be designed with stops in the threads that limit how far stylet 20 can retract relative to catheter tube 10. For example, the amount of retraction may be limited to just within catheter tube 10 for efficient deployment of stylet 20. Another feature of a threaded interface is that the risk of accidentally exposing the tip is eliminated because the user must intentionally actuate stylet 20 by rotating handle 30 in order to advance stylet 20. According to embodiments, handle 30 may be actuated by a motorized device that rotates stylet 20 designed with threads or linearly advances stylet 20 without threads. Other types of interfaces are contemplated, including spring-loaded, pressure activated, hydraulically-powered, interfacing gears, etc.

According to embodiments, after puncturing a balloon system, fluid may be aspirated from the balloon system through or into catheter tube 10 via an aspiration hole when at least a portion of stylet 20 is advanced beyond the distal opening of catheter tube 10.

Figure 2:
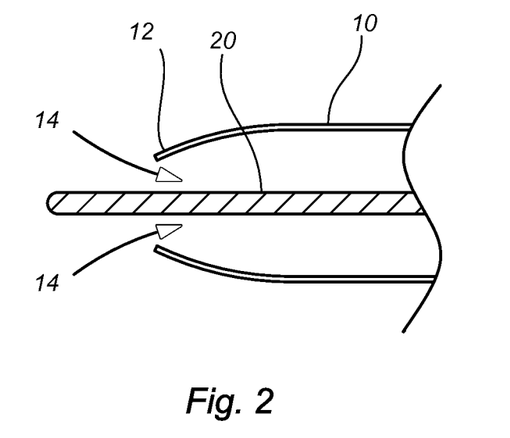
FIG. 2 shows a cross sectional view of a catheter tube with stylet.

According to embodiments, as shown in FIG. 2, gaps 14 may be provided at or near the distal end of catheter tube 10 for aspiration between catheter tube 10 and stylet 20, as shown in FIG. 2. For example, the distal opening that accommodates stylet 20 may also be used for aspiration, as shown in the left side of FIG. 2. Gaps 14 may be effective as the portion containing the same is advanced beyond the wall of the balloon and into the interior thereof.

Figure 3:
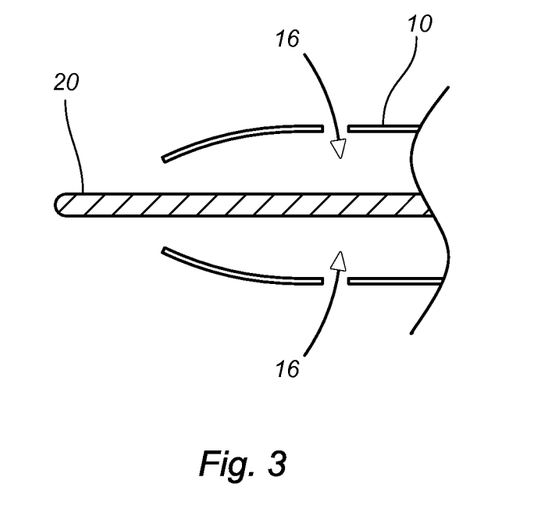
FIG. 3 shows a cross sectional view of a catheter tube with stylet.

According to embodiments, as shown in FIG. 3, catheter tube 10 is designed with side holes 16 along the length thereof, such that fluid may be suctioned into catheter tube 10 even when stylet 20 is fully or partially occluding the distal tip opening. Side holes 16 may be effective as the portion containing the same is advances beyond the wall of the balloon and into the interior thereof.

According to embodiments, devices and components may be configured for use within a scope device, such as a gastroscope or endoscope. Various dimensions of such a system may be used and customized based on the needs of the application and the use. For example, for use through a 2.8 mm diameter gastroscope channel, catheter tube 10 may have an outer diameter of about 0.100" to about 0.107", an inner diameter of about 0.070" to about 0.086", and a length of about 50" to about 75". Markings may be printed on the distal section of the catheter to indicate the 1 cm and 2 cm mark of the catheter. By further example, stylet 20 may have a wire diameter of about 0.030" to about 0.040" and a coring tip diameter of about 0.040" to about 0.052". According to embodiments, stylet 20 may be constructed of a custom wire rope (e.g. the Helical Hollow Strand®, Fort Wayne Metals, Inc., Fort Wayne, Ind.), which has superior column strength and translates rotation better than standard wire rope. Such a stylet wire design ensures a consistent coring motion at the tip for successful puncture of the balloon system without tearing the balloon skin.

According to embodiments, stylet 20 may have one or more of a variety of designs and configurations. Stylet 20 may have a needle tip configuration taking the shape of a coring needle, a sharpened conical point, or a sharpened beveled point. Other geometries and shapes are contemplated as effective for achieving the results disclosed herein, as recognized by those having ordinary skill in the art.

Figure 4A:
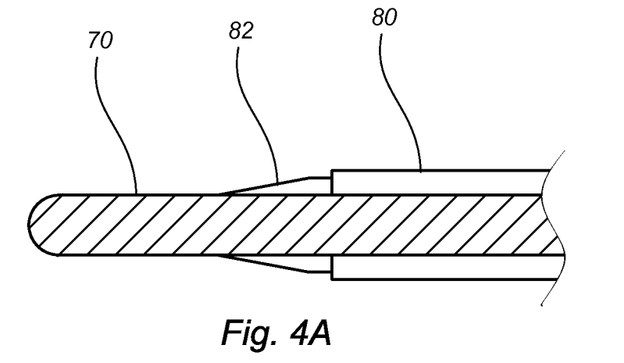
FIG. 4A shows a cross sectional view of a needle device with obturator in an extended state.
Figure 4B:
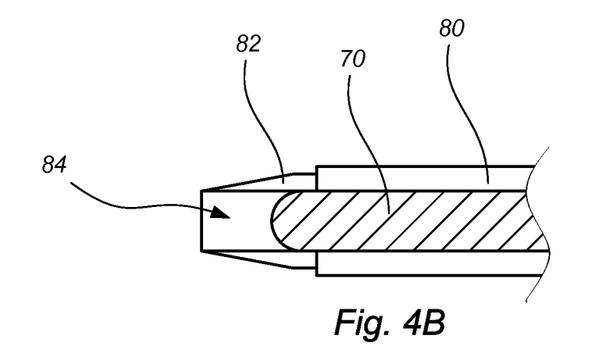
FIG. 4B shows a cross sectional view of a needle device with obturator in a retracted state.

According to embodiments, as shown in FIG. 4, hollow needle device 80 and obturator 70 are disclosed. Hollow needle device 80 includes channel 84, with obturator 70 disposed therein. Needle device 80 may be sheathed within an introducer tube for efficient delivery through an endoscope. For example, needle device 80 may be within the lumen of catheter tube 10.

Figure 5:
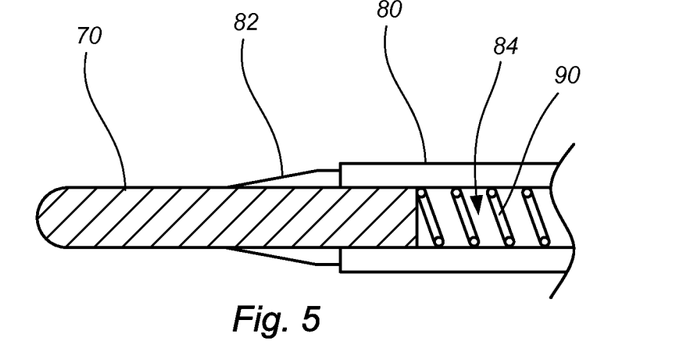
FIG. 5 shows a cross sectional view of a needle device with obturator in an extended state.

According to embodiments, obturator 70 may be configured to provide a smooth transition at needle tip 82, such that it may be delivered to the balloon system without harming the patient or damaging the endoscope while obturator 70 is in an extended state (shown in FIGS. 4A and 5). In the extended state, at least a portion of obturator 70 is extended beyond the distal end of needle tip 82, such that a sharpened portion of needle tip 82 is not exposed, but rather made into part of a smooth transition.

According to embodiments, catheter tube 10 may provide the features of needle device 80, as disclosed herein. According to embodiments, catheter tube 10 may include needle tip 82 at a distal end thereof, wherein catheter tube 10 is configured to puncture a balloon wall. According to embodiments, catheter tube 10 may house stylet 20 or obturator 70 in a lumen thereof, with features as disclosed herein.

According to embodiments, catheter tube 10 may be a delivery system, such as an endoscope, gastroscope, etc., wherein devices housed therein may be advanced to provide features and functionality at an operation location.

According to embodiments, obturator 70 may be retracted to a retracted state, as shown in FIG. 4B. In the retracted state, needle tip 82 is more exposed and capable of puncturing a target, as the smooth transition to obturator 70 has been removed. Retraction of obturator 70 activates the cutting, coring, puncturing, or other functionality of the needle tip. Obturator 70 may be retracted by a variety of methods. For example, the balloon wall may push obturator 70 back against a spring 90 as shown in FIG. 5. Obturator 70 may be retracted manually via a portion accessible at a proximal end by a user. Obturator 70 may be retracted by relatively low pressure applied to channel 84 relative to pressure exterior to channel 84.

According to embodiments, a method to puncture and deflate a balloon system using devices, systems, and components described herein is disclosed. According to embodiments, suction tubing from a pump is connected to suction port 50 of the device's y-connector. At the user's discretion, suction may be started prior to or after inserting the catheter into the balloon system.

According to embodiments, the device is delivered through the instrument channel of an endoscope to the implanted balloon system. With the distal end of stylet 20 retracted relative to the distal end of catheter tube 10, the catheter is positioned perpendicular against the surface of the balloon system. The user then rotates handle 30 or otherwise actuates stylet 20 to rotate and/or advance stylet 20. The tip of stylet 20 contacts and punctures the balloon skin.

According to embodiments, the user advances the catheter to insert the device at least partially through the puncture. At this point, fluid may be aspirated from the inside of the balloon through gaps 14, side holes 16, or other fluid connections from within the balloon device. After the first balloon has been sufficiently deflated, handle 30 is rotated in the opposite direction or otherwise actuated to retract stylet 20 relative to catheter tube 10. Catheter tube 10 is then removed from the balloon.

According to embodiments, where needle device 80 is delivered via catheter tube 10, needle device 80 may be activated and operated as disclosed herein to puncture a balloon in combination with aspiration operations to evacuate fluid from within the balloon.

According to embodiments, the device may be repositioned against another balloon and the procedure may be repeated to puncture and suction fluid from additional balloons. The operations may be performed in the above or any variety of sequences that provides the desired results.

According to embodiments, a kit of parts is disclosed, including components disclosed herein, for use by a user. Included in the kit may be instructions for use.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A method of deflating a balloon, comprising:
   providing a deflation catheter device comprising a catheter tube having a lumen and a stylet within the catheter tube;
   delivering the deflation catheter to an implanted balloon device with the stylet being retracted relative to the distal end of the catheter tube;
   positioning the catheter tube against a surface of the implanted balloon device;
   actuating a handle to advance the stylet relative to the catheter tube and the implanted balloon device, whereby the stylet contacts and punctures a wall of the implanted balloon device;
   advancing at least a portion of the catheter tube through the wall of the implanted balloon device; and
   aspirating fluid from within the implanted balloon device through the lumen from a distal end thereof to a suction port at a proximal end of the lumen without removing the stylet from the catheter tube.

2. The method of claim 1, wherein actuating the handle simultaneously rotates the stylet.

3. The method of claim 1, further comprising: retracting the stylet within the lumen to be concealed by the distal end of the lumen.

4. The method of claim 1, further comprising: removing the deflation catheter from the balloon.

5. The method of claim 1, further comprising: reusing the deflation catheter to deflate additional balloons without reloading the stylet into the catheter tube.

6. The method of claim 4, further comprising: retrieving the implanted balloon device from an implant location.

* * * * *